US005624938A

United States Patent [19]
Pernis

[11] Patent Number: 5,624,938
[45] Date of Patent: Apr. 29, 1997

[54] USE OF CHLOROQUINE TO TREAT MULTIPLE SCLEROSIS

[75] Inventor: Benvenuto G. Pernis, Bronxville, N.Y.

[73] Assignee: The Trustees of Columbia University in the City of New York, New York, N.Y.

[21] Appl. No.: 276,259

[22] Filed: Jul. 18, 1994

[51] Int. Cl.$^6$ ............................ A01N 43/42; A61K 31/47
[52] U.S. Cl. ........................ 514/313; 514/2; 514/789; 514/825; 514/885; 514/886; 514/889; 514/903
[58] Field of Search ..................... 514/825, 885, 514/903, 886, 313, 889, 789, 2

[56] References Cited

U.S. PATENT DOCUMENTS

| | | | |
|---|---|---|---|
| 2,233,970 | 3/1941 | Andersag et al. | 260/285 |
| 4,806,537 | 2/1989 | Roberts | 514/825 X |
| 4,831,033 | 5/1989 | Roberts | 514/825 X |
| 5,149,688 | 9/1992 | Ando et al. | 514/313 X |
| 5,183,687 | 2/1993 | Hunter | 514/313 X |
| 5,234,683 | 8/1993 | Hunter et al. | 514/313 X |

OTHER PUBLICATIONS

Arnason, B.G.W. (1993) Interferon Beta in Multiple Sclerosis, *Neurology* 43:641–643 (Exhibit 3).
Augustijns, P., et al. (1992) Chloroquine Levels in Blood During Chronic Treatment Of Patients with Rheumatoid Arthritis, *Eur. J. Clin, Pharmacol* 42:429–433 (Exhibit 4).
Brooks, P.M. et al. (1986) Slow–acting Anti–Rheumatic Drugs, *The Clinical Pharmacology of Anti–Inflammatory Agents* eds. Taylor and Franers, London, pp. 86–91 (Exhibit 5).
Clark, P., et al. (1993) Hydroxychlorquine Compared with Placebo in Rheumatoid Arthrisis, *Ann. Intern. Med.* 119:1067–1071 (Exhibit 6).
Connolly, K.M., et al. (1988) alteration of Interleukin Activity and the Acute Phase Response in Adjuvant Arthritis Rats Treated with Disease Modifying Antirheumatic Drugs, *Agents and Actions* 25:94–105 (Exhibit 7).
Edelson, R.L. (1991) Photopheresis: A Clinically relevant Immunobiologic Response Modifier, *Ann. N.Y. Acad. Sci* 636:154–164 (Exhibit 8).
Fowler, P.D. et al. (1984) Report on Chloroquine and Dapsone in the Treatme Of Rheumatoid Arthritis: A 6–Month Comparative Study, *Ann. Rheum. Dis.* 43:200–204 (Exhibit 9).
Fox, R.I. (1993) Mechanism of Action Of Hydroxychloroquine as an Artirheumat Drug, *Sem Arthr. Rheum.* 23:82–91 (Exhibit 10).
Gaur, A., et al. (1993) Requirement for CD8+ Cells in T Cell Receptor Peptide–Induced Clonal Unresponsiveness, *Science* 259:91–94 (Exhibit 11).
Gautum, A.M. and Glynn, P. (1989) Lewis Rat Lymphoid Dendritic cells Can Efficiently Present Homologous Myelin Basic Protein to Encephalitogenic Lymphocytes, *J. Neuroimmun* 22:113–121 (Exhibit 12).
Gilman, A.G., et al. (1990) *Goodman and Gilman's: The Pharmacological Basis of Therapeutics*, 8th ed., New York, pp. 981–983 (Exhibit 13).

Howell, M.D., et al. (1989) Vaccination Against Experimental Allergic Encephalomyelitis with T Cell Receptor Peptides, *Science* 246:668–670 (Exhibit 14).
Hurvitz, D. and Hirschhorn, K. (1965) Suppression of In vitro Lymphocyte responses by Chloroquine, New engl. J. Med. 273:23–26 (Exhibit 15).
IFNB Multiple Sclerosis Study Group (1993) Interferon Beta 1–b is Effective in Relapsing–Remitting Multiple Sclerosis. I., *Neurology* 43:655–661 (Exhibit 16).
Jack, A.S., et al. (1990) Cutaneous T–Cell Lymphoma Cells Employ a Restricted Range of T–Cell Antigen Receptor Variable Region Genes, *Am. J. Pathol.* 136:17–21 (Exhibit 17).
Jacobs, L., et al., (1987) Intrathecally Administered natural Human Fibroblas Interferon Reduces Exacerbations on Multiple Sclerosis, *Arch. Neurol.* 44:589–595 (Exhibit 18).
Jaing, H., et al. (1992) Role of CD8+ t Cells in Murine Experimental Allergi Encephalomyelitis, *Science* 256:1213–1215 (Exhibit 19).
Kawabe, Y. and Ochi, A. (1991) Programmed Cell Death and Extrathymic Reducti Of V Beta 8+ CD4+ T Cells in Mice tolerant to *Staphylococcus aureus* Enterotoxin B, *Nature* 349:245–249 (Exhibit 20).

(List continued on next page.)

Primary Examiner—Paul F. Shaver
Attorney, Agent, or Firm—John P. White

[57] ABSTRACT

This invention provides a pharmaceutical composition which comprises an amount of chloroquine effective to block MHC Class I recycling and an amount of a CD8+ T cell stimulatory agent effective to stimulate proliferation of CD8+T cells to a concentration such that the resulting CD8+ T cells kill CD4+ T cells, and a pharmaceutically acceptable carrier.

This invention provides a method for treating an autoimmune disease in a subject which comprises administering to the subject an amount of chloroquine effective to treat the autoimmune disease.

This invention provides a method for treating cutaneous lymphoma disease in a subject which comprises administering to the subject an amount of chloroquine effective to treat the cutaneous lymphoma disease.

This invention provides a method for treating rheumatoid arthritis in a subject which comprises administering to the subject an amount of the pharmaceutical composition of chloroquine and a CD8+T cell stimulatory agent effective to treat rheumatoid arthritis.

Finally, this invention provides a method of depleting CD4+ T cells which comprises contacting to the cells an amount of chloroquine effective to block MHC Class I recycling and a CD8+ T cell stimulatory agent in an amount effective to stimulate proliferation of CD8+ T cells to a concentration such that the resulting CD8+T cells kill CD4+T cells, so as to thereby deplete CD4+ T cells.

28 Claims, 3 Drawing Sheets

OTHER PUBLICATIONS

Kawabe, Y. and Ochi, A. (1990) Selective Anergy of V Beta+, CD+4 T Cells in Staphyloccoccus Enterotozin B–Primed Mice, *J. Exp. Med.* 172:1065–1070 (Exhibit 21).

Koh, d. et al. (1992) Less Mortality But More Relapses in Experimental Allergic Encephalomyelitis in Cd8+–/–Mice, *Science* 256:1210–1213 (Exhibit 22).

Lipsky, P.E. (1983) Remission–Inducing Therapy in Rheumatoid Arthritis Am. J. Med. Oct. 31, 1983:40–49 (Exhibit 23).

Mackenzie, A.H. (1983) Dose Refinements in Long–Term Therapy of Rheumatoid Arthritis with Antimalarials, *Am. J. Med.* Jul. 18, 1983:40–45 (Exhibit 24).

Maksymowych, W. and Russell, A.S. (1987) Antimalarials in Rheumatology: Efficacy and Safety, *Sem. Arthr. Rheum.* 16:206–221 (Exhibit 25).

Noronha, A., et al. (1990) Interferon Beta Augments Suppressor Cell Funtio in Multiple Sclerosis, *Ann. Neurol.* 27:207–210 (Exhibit 26).

Paty, D.W. et al. (1993) Interferon beta–1b is Effective in Relapsing–Remitting Multiple Sclerosis, *Neurology* 43:662–667 (Exhibit 27).

*Physicians' Desk Reference* (1992) 46th ed. New Jersey, pp. 2067–2069 (Exhibit 28).

Reid, P.A. and Watts C. (1990) Cycling of Cell–Surface MHC Glycoproteins Through Primaquine–Sensitive Intracellular Compartments, *Nature* 346:655–657 (Exhibit 29).

Rekant, S.I. and Becker, L.E. (1973) Auto–Immune Annular Erythema, *Arch. Dermatol.* 107:424–426 (Exhibit 30).

Rellahan, B.L., et al. (1990) In Vivo Induction of Anergy in Peripheral V Beta 8+T Cells by Staphylococcal Enterotoxin B, *J. Exp. Med.* 172:1091–1100 (Exhibit 31).

Salmeron, G. and Lipsky, P.E. (1983) Immunosuppressive Potential of Antimalarials, *Am. J. Med.* 75:19–24 (Exhibit 32).

Sperber, K., et al. (1993) Selective Regulations of Cytokine Secretion by Hydroxychloroquine: Inhibition of Interleukin 1 Alpha (IL–1–alpha) and IL–6 in Human Monocytes and T Cells, *J. Rheum.* 20:803–808 (Exhibit 33).

Sun, D., et al. (1988) Suppression of Experimentally Induced Autoimmune Encephalomyelitis by cytolytic T—T Cell Interactions, *Nature* 332:843–845 (Exhibit 34).

Titus, E.O. (1989) Recent Developments in the Understanding of the Pharmacokinetics and Mechanism of Action of Chloroquine, *Ther. Drug. Monit.* 11:369–379 (Exhibit 35).

Tse, D.B., et al. (1986) Recycling Class I MHC Antigens: Dynamics of Internalization, Acidification, and Ligand–Degradation in Murine T Lymphoblasts, *J. Mol. Cell Immunol.* 2:315–329 (Exhibit 36).

Vandenbark, A.A. et al. (1989) Immunization with a Synthetic T–Cell Receptor V–Region Peptide Protects Against Experimental Autoimmune Encephalomyelitis, *Nature*, 341:541–544 (Exhibit 37).

USE OF CHLOROQUINE TO TREAT MULTIPLE SCLEROSIS

Throughout this application, various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THE INVENTION

Multiple sclerosis (MS) is a common neurologic disease that is a major cause of disability and economic loss, especially in young adults. MS is confined to the central nervous system in which demyelination and inflammation in the brain, the presence of oligoclonal bands, and activated cells in cerebrospinal fluid are characteristic features [28, 31, 34]. Extensive research has failed to identify the cause of MS. Although many therapies have been used, none has significantly reduced exacerbation rates, the accumulation of disability, and the increase in MS lesion burden as judged by cranial MRI.

A recent multicenter epidermological study [36] has shown clear benefits of prolonged treatment of patients with MS with recombinant human beta-1 interferon (β-IFN) [2, 10, 14, 27, 30]. These benefits are, however, limited so that the conclusion has been drawn that "β-IFN is not the long-awaited cure of M.S" [1].

Antimalarial drugs [22, 23], such as chloroquine [25] and hydroxychloroquine, have been used for many years in the treatment of rheumatoid arthritis, and systemic lupus erythematosus. The effect of chloroquine in rheumatoid arthritis [39] has been ascribed to an anti-inflammatory action mediated by an inhibition of the release of interleukin-1 from the monocytes [4, 5], however, this is not supported by recent investigations [5, 40].

SUMMARY OF INVENTION

This invention provides a pharmaceutical composition which comprises an amount of chloroquine effective to block MHC Class I recycling and an amount of a CD8+ T cell stimulatory agent effective to stimulate proliferation of CD8+T cells to a concentration such that the resulting CD8+ T cells kill CD4+T cells, and a pharmaceutically acceptable carrier.

This invention provides a method for treating an autoimmune disease in a subject which comprises administering to the subject an amount of chloroquine effective to treat the autoimmune disease.

This invention provides a method for treating cutaneous lymphoma disease in a subject which comprises administering to the subject an amount of chloroquine effective to treat the cutaneous lymphoma disease.

This invention provides a method for treating rheumatoid arthritis in a subject which comprises administering to the subject an amount of the pharmaceutical composition of chloroquine and the CD8+T cell stimulatory agent effective to treat rheumatoid arthritis.

Finally, this invention provides a method of depleting CD4+ T cells which comprises contacting to the cells an amount of chloroquine effective to block MHC Class I recycling and a CD8+T cell stimulatory agent in an amount effective to stimulate proliferation of CD8+ T cells to a concentration such that the resulting CD8+T cells kill CD4+ T cells, so as to thereby deplete CD4+ T cells.

BRIEF DESCRIPTION OF THE FIGURES

FIGS. 1A–1B CD8+ T cell depletion protects Vβ8.1,2+ CD4+ T cells from "superantigen" Enterotoxin B from *Staphyloccus aureas* (SEB) induced T cell death. Balb/C mice were injected in the tail vein on day 1 with either 50 µg SEB in 0.1 ml PBS (SEB) or PBS alone (PBS). Seven days before SEB/PBS injections one group of mice were CD8+ T cell depleted. On days 4, 7, 14 and 21 after peripheral blood drawn from the tail vein of 4–6 mice in each group was pooled, mononuclear cells purified on a lymphocyte separation medium gradient and stained with the following monoclonal antibodies: fluorescein 53-6.72 [anti-CD8]; Allophycocyanin GK1.5 [anti-CD4]; and biotin KJ-16 [anti-Vβ8.1,2]; or biotin RR4.7 [anti-Vβ6].

FIG. 2 The effects of treatment on the percentage of CD4+ cells expressing Vβ8+ T cell receptor chain. Six groups of Balb/c mice (6 mice each) were treated as follows: 1) daily injections of PBS (phosphate buffered saline) for 14 days (●—●, Control) 2) daily injections of 1 mg chloroquine base (0——0, CHQ) 3) One i.v. injection of 50 µg SEB on day 0 (△—△, SEB) 4) daily injections of 1 mg chloroquine base, plus one i.v. injection of 50 µg SEB on day 0 (x——x, SEB-CHQ) 5) 50 µg SEB on day 0 mice depleted of CD8+ T cells, depletion performed as described in reference 4 (□——□, CD8 depleted SEB) 6) 50 µg SEB on day 0 in mice depleted of CD8+ T cells and treated with daily injections of 1 mg chloroquine base (†——†, CD8 depleted-SEB-CHQ).

DETAILED DESCRIPTION OF THE INVENTION

This invention provides a pharmaceutical composition which comprises an amount of chloroquine effective to block MHC Class I recycling and an amount of a CD8+ T cell stimulatory agent effective to stimulate proliferation of CD8+T cells to a concentration such that the resulting CD8+ T cells kill CD4+T cells, and a pharmaceutically acceptable carrier.

In one embodiment of the composition above or the methods below the amount of chloroquine is from about 200 to about 600 mg/day. In another embodiment the amount is from about 300 to about 500 mg/day. In the preferred embodiment the amount is 400 mg/day. The amount of chloroquine effective to block MHC Class I recycling is known to those skilled in the art.

The "proliferation of CD8+ T cells" is defined herein as the increase in the molar concentration, or activity, of CD8+ T cells such that the resulting increase in the molar concentration, or activity, of CD8+T cells is effective to kill CD4+ T cells. The molar concentration of CD8+ T cells necessary to kill CD4+ T cells is known to those skilled in the art. The molar concentration may be in an absolute number or quantitative relationship.

In one embodiment the CD8+T cell stimulatory agent is interferon. In another embodiment the CD8+ T cell stimulatory agent is β-interferon. Other CD8+ T cell stimulatory agents include, but are not limited to: vaccination with CD4+ T cells, solid anti-CD8, Fc gamma-globulin, photopheresis, IL-10, or combinations thereof. Other CD8+ T cell stimulatory agents are known to those skilled in the art.

In one embodiment of the composition above or the methods below the amount of β-interferon is from about 750,000 units (IU) to about $1\times10^7$ units. In another embodiment the amount of β-interferon from about $1\times10^6$ units to about $9\times10^6$ units. In a preferred embodiment the amount of β-interferon is $8\times10^6$ units. The amount of β-interferon may vary depending on the condition and weight of the subject.

This invention provides a method for treating an autoimmune disease in a subject which comprises administering to the subject an amount of chloroquine effective to treat the autoimmune disease.

As defined herein an "autoimmune disease" is a disease in which the body produces an immunologic response against itself. Autoimmune diseases include, but are not limited to: Hashimoto's thyroidiris, pernicious anemia, Addison's disease, insulin-dependent diabetes mellitus, Goodpasture's syndrome, dermatomyositis, scleroderma, and sympathetic ophthalmia. In the preferred embodiment the autoimmune disease is multiple sclerosis.

In one embodiment, treatment further comprises administering to the subject a CD8+ T cell stimulatory agent in an amount effective to stimulate proliferation of CD8+ T cells to a concentration such that the resulting CD8+ T cells kill CD4+ T cells in the subject.

Further, in one embodiment the CD8+ T cell stimulatory agent is interferon. In another embodiment the interferon is β-interferon. Other CD8+ T cell stimulatory agents have been demonstrated hereinabove.

This invention provides a method for treating cutaneous lymphoma disease in a subject which comprises administering to the subject an amount of chloroquine effective to treat the cutaneous lymphoma disease.

In one embodiment chloroquine is administered further to treatment of photopheresis. As defined herein "photopheresis" is an immune response modifier by which peripheral blood is exposed in an extracorpreal flow system to photoactivated 8-methoxypsoralen (8-MOP). Methods in which photopheresis are employed are known to those skilled in the art.

This invention provides a method for treating rheumatoid arthritis in a subject which comprises administering to the subject an amount of the pharmaceutical composition of chloroquine and the CD8+ T cell stimulatory agent effective to treat rheumatoid arthritis.

This invention provides a method of depleting CD4+ T cells which comprises contacting to the cells an amount of chloroquine effective to block MHC Class I recycling and a CD8+ T cell stimulatory agent in an amount effective to stimulate proliferation of CD8+ T cells to a concentration such that the resulting CD8+ T cells kill CD4+ T cells, so as to thereby deplete CD4+ T cells.

In one embodiment the CD4+ T cells are pretreated with an antigen prior to chloroquine administration. In another embodiment the CD4+ T cells are pretreated with a mitogen prior to the chloroquine administration. The antigen includes, but is not limited to: *Staphyloccus aureus* (SEB), pokeweed mitogen (PwM), phytohaemagglutinin (PHA), lipopolysaccharide (LPS), or concanavalin A (Con A).

The subject may be a mammal, or more specifically a human, horse, pig, rabbit, dog, monkey, or rodent. In the preferred embodiment the subject is a human.

As used herein the "amount" of chloroquine is the amount effective to alleviate or cure the subject with multiple sclerosis, cutaneous lymphoma or rheumatoid arthritis as hereinabove indicated.

As is known to those skilled in the art effective amounts vary with the type of therapeutic agent. Further, it is known to those skilled in the art how to determine an effective amount of a suitable therapeutic agent.

Further, this invention includes, but is not limited to, derivatives of chloroquine such as: chloroquine phosphate, chloroquine diphosphate, chloroquine sulphate, hydroxychloroquine sulphate, or derivatives thereof. As defined herein "hydroxychloroquine" is a β-hydroxylated N-ethyl substituent of chloroquine.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration. In one embodiment the chloroquine and β-IFN are administered sequentially. In another embodiment the chloroquine and β-IFN are administered simultaneously.

As used herein administration means a method of administering to a subject. Such methods are well known to those skilled in the art and include, but are not limited to: administration topically, parenterally, orally, intravenously, intramuscularly, subcutaneously or by aerosol. Administration may be effected continuously or intermittently such that the therapeutic agent in the subject is effective to treat a subject with multiple sclerosis.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Material and Methods

Balb/C mice (8–12 weeks old) were obtained front the Jackson Laboratory. Anti-Vβ6 were obtained from Pharmingen (San Diego). All other staining reagents were prepared in as previously described [8]. Dead cells were excluded using propidium iodide [29]. Flow cytometric analysis was performed on a dual laser FACStar$^{Plus}$ (Becton-Dickinson, San Jose) using FACS/DESK data analysis software (Stanford University) [26] as previously described.

Experiment 1: Demonstration of CD8+ T Cells that Selectively Kill CD4+ Target Lymphocytes that Express a Given Chain of the T Cell Receptor.

Administration of the "superantigen" Enterotoxin B from *Staphyloccus aureus* (SEB) to adult mice, is regularly followed by a series of events that affect mostly the T lymphocytes that express receptors of the Vβ8+ CD4+ T cells and a state of non-reactivity of the remaining. Collectively these events develop within 10–15 days [17] and determine a state of "tolerance" to the superantigen. CD8+T cells play a role in the negative immunoregulation (suppression) that follows one episode of acute allergic encephalomyelitis (EAE) in mice by acting on the pathogenic CD4+ T cells [15], and therefore it was investigated whether these cells are also involved in the peripheral tolerance that follows treatment with SEB [19, 35]. Results indicated that depletion of CD8+ T lymphocytes completely eliminates the deletion of Vβ8+ T cells induced by SEB.

Depletion of CD8+ T cells was obtained with the administration of the monoclonal rat anti CD8+ antibody 53-6.72, a depletion which is almost complete, in the blood as well as in the lymphoid tissues, for over 10 days. This time window of antibody-mediated deplemion of CD8+T cells is sufficient to cover the series of events that follow the administration of SEB in adult mice.

Peripheral tolerance induced by SEB consists of two cellular events, as shown by other groups [17, 18, 33] T cell death, preceded by clonal expansion, and T cell anergy. To test if CD8+ T cells are involved in SEB induced T cell death, 50 μg SEB was injected intravenously into both untreated and CD8+ T cell-depleted Balb/C mice, then the portion of Vβ8.1,2+ CD4+ T cells (which are specifically interactive with SEB) in peripheral CD4+ T cells of those mice was determined.

Figure 1A:
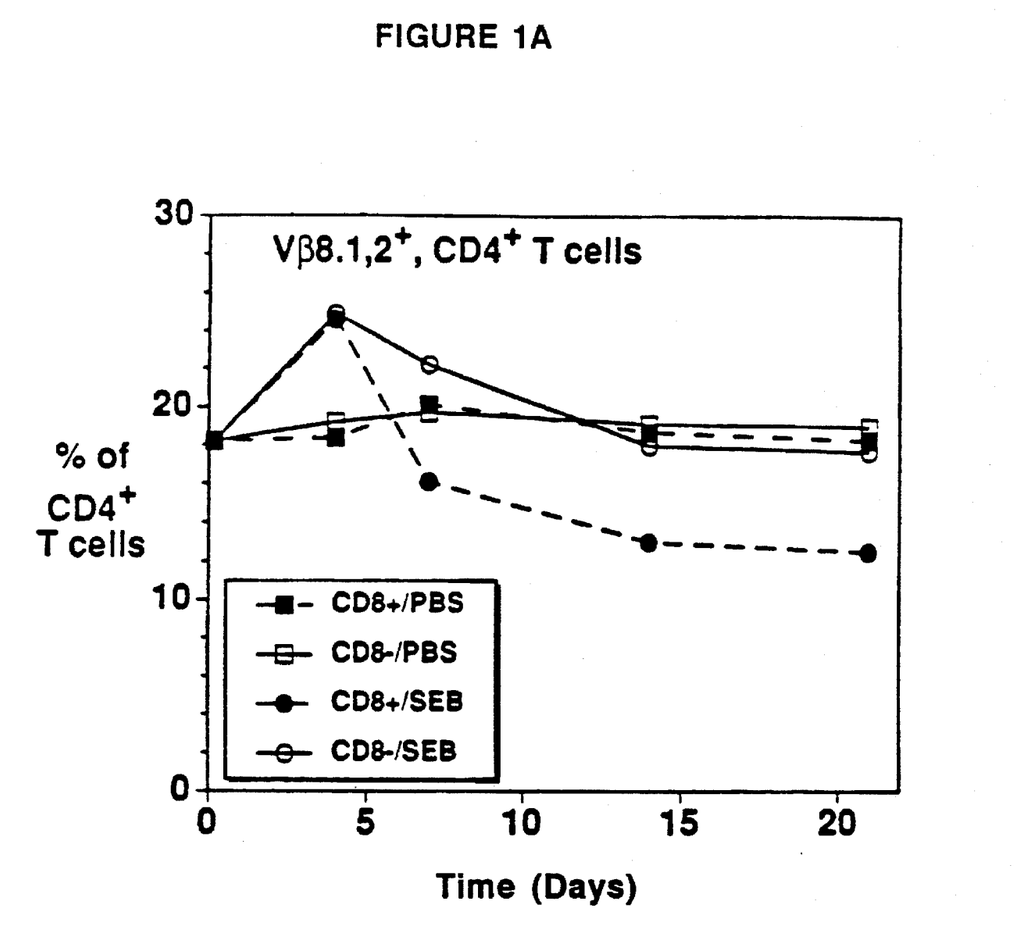

As shown by FIG. 1A and Table 1, in CD8+ T cell nondepleted, SEB primed group Vβ8.1,2+ CD4+ T cells decreased from a day 4 of SEB injection, reached the lowest point between day 7 and day 14, and remained low for at least another week. The T cell death was preceded by expansion of the Vβ8.1,2+ CD4+ T cell population which reached the peak on day 4. On the other hand in CD8+T cell depleted mice treated with SEB, the number of Vβ8.1,2+ CD4+ T cells was increased after SEB injection, reached the peak on day 4, and slowly returned to normal levels by day 14. The fall below normal levels by day 14. The fall below normal levels (25–28%) in the percentage of Vβ8 1,2+ CD4+ T cells that is observed in normal mice treated with SEB, was completely eliminated by depletion of CD8+ T cells. Both SEB induced T cell death and the protection due to CD8+ T cell depletion are TCR Vβ-specific, since there was no difference of the numbers of Vβ6+ CD4+ T cell population between CD8+ T cell non-depleted and CD8+ T cell depleted, SEB primed mice as shown in FIG. 1B.

Figure 1B:
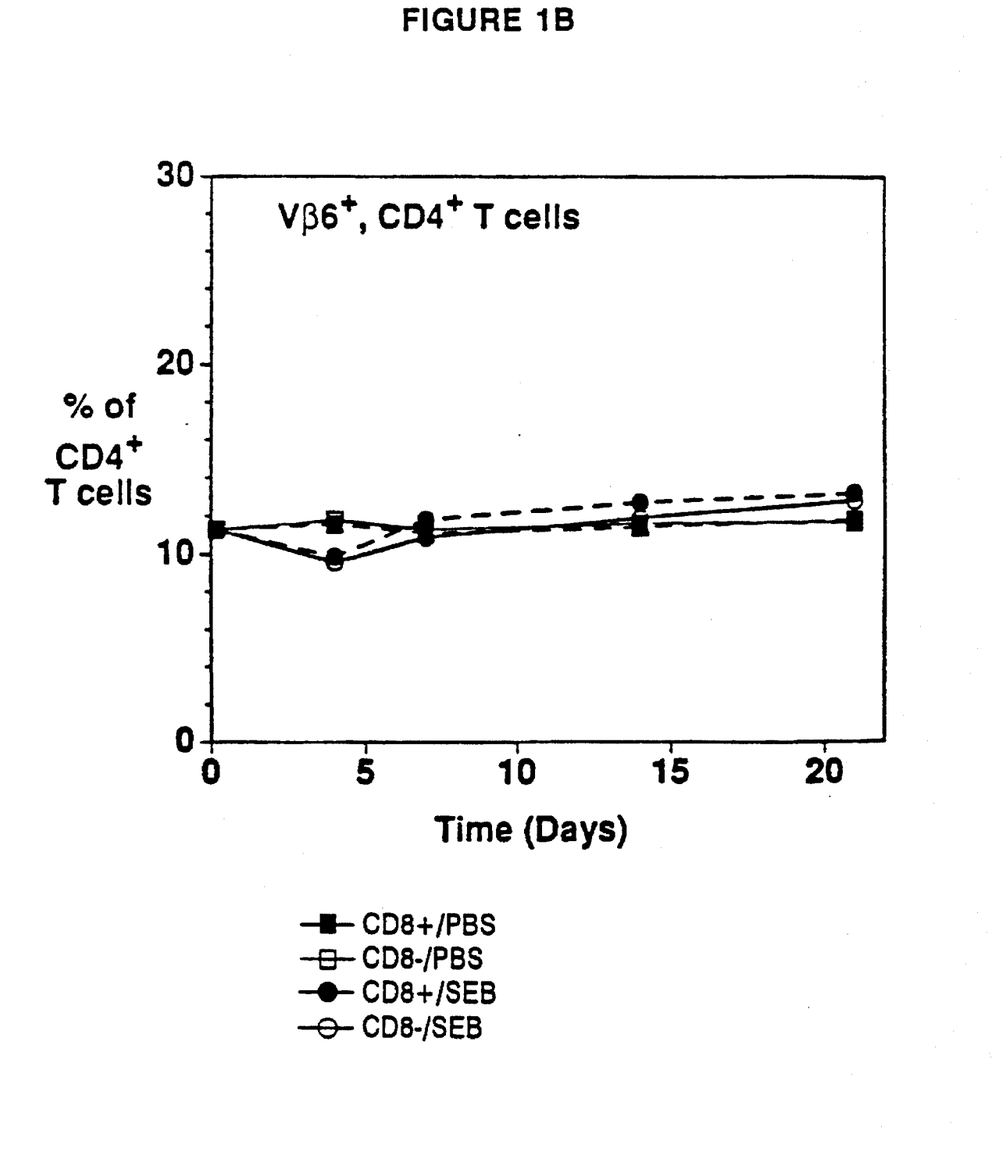

CD8+ T cell depletion protects Vβ8.1,2+ CD 4+ T cells from SEB induced T cell death (FIGS. 1A and 1B). Balb/C mice (8–12 weeks old, Jackson Laboratory) were injected in the tail vein on day 1 with either 50 μg SEB (Toxin Technology, Madison, Wis.) in 0.1 ml PBS (SEB) or PBS alone (PBS). Seven days before SEB/PBS injections one group of mice were CD8 T cell depleted. On days 4, 7, 14 and 21 after peripheral blood drawn from the tail vein of 4–6 mice in each group was pooled, mononuclear cells purified on a lymphocyte separation medium gradient (Organon Technicka) and stained with the following monoclonal antibodies: fluorescein 53-6.72 [anti-CD8] [20]; Allophycocyanin GK1.5 [anti-CD4] [6]; and biotin KJ-16 [anti-Vβ8.1,2] [16] or biotin RR4.7 [anti-Vβ6] [9]. Biotin conjugates were revealed with Texas Red-Avidin.

The data is expressed as the percent of total CD4+ or total CD8+ T cells. The values for day 1 are the average of >50 normal animals. For days 4, 7, 14 and 21, each point represents the average of three separate experiments with 4–6 mice per group per experiment. The group designations are: CD8+/PBS, PBS-primed, CD8 T cell non-depleted; CD8-/PBS, PBS-primed, CD8 T cell depleted; CD8+/SEB, SEB-primed, CD8 T cell non-depleted; CD8-/SEB, SEB-primed, CD8 T cell depleted.

The fact that the death of Vβ8+ CD 4+ T cells that follows the initial expansion of these cells in mice treated with SEB requires the presence of CD8+T cells indicates that the Vβ8 CD4+ T cells that were stimulated by SEB in the first place induced a population of CD8+ killers with anti Vβ specificity (distinct from the Vβ8 CD8+ cells directly stimulated by SEB), that was ultimately responsible for the partial deletion of Vβ8+ CD 4+ T cells.

TABLE 1

Analysis of Vβ8.1,2+, Vβ6+ expression by T cells in CD8 T cell non-depleted and CD8 T cell depleted SEB primed Balb/C mice

| | % of Positive Cells/Total of | | | |
|---|---|---|---|---|
| | CD4+ T cells | | CD8+ T cells | |
| | Vβ8.1,2 | Vβ6 | Vβ8.1,2 | Vβ6 |
| CD8+/PBS | 18.7 +/− 0.84 | 11.4 +/− 0.20 | 25.5 +/− 0.49 | 12.1 +/− 1.40 |
| CD8−/PBS | 19.1 +/− 0.20 | 11.6 +/− 0.32 | | |
| CD8+/SEB | 13.0 +/− 2.40 | 12.7 +/− 0.44 | 29.1 +/− 4.80 | 11.6 +/− 2.97 |
| CDB−/SEB | 18.0 +/− 0.31 | 11.9 +/− 0.90 | | |

Table 1 shows the percentage of Vβ8+and Bβ6+ T cells amongst total CD4 or CD8 T cells in peripheral blood of CD8 T cell non-depleted (CD8+/SEB) and CD8 T cell depleted (CD8−/SEB) mice 14 days after SEB injection. Experiments were done as in FIGS. 1A–1B. Each value represents (average±Standard Deviation) data from 12–18 mice of three separate experiments (4–6 mice per experiment).

Results indicate that directly show specific killing in vitro of syngeneic CD4+Vβ8+ T cells by lines of CD8+ T lymphocytes obtained from the spleens of mice primed two weeks previously with SEB.

Experiment 2: Establishing Different CD4+Vβ8+ T Cell Lines in B10PL Mice

CD4+ T cells are purified from spleen and lymphnodes of B.10.PL mice by depleting B cells and CD8+T cells with rat anti-mouse Mab 53-6.72 and goat anti-rat coated magnetic beads. CD4+ Vβ8+ and CD4+ Vβ8− T cells are obtained by staining the CD4+ T cells with anti-mouse Vβ8 Mab F23.1 and being separated by goat anti-mouse coated beads. CD4+ and Vβ8.2+ T cells and mixture of CD4+ Vβ8+ and CD4+ Vβ8.3+ T cells are obtained from the mixture of these two types of the cells by using anti-mouse Vβ8.1 and Vβ8.2 Mab KJ-16. The phenotypes of the CD4+ T cell lines are as follows:

|       | F23.1 | KJ-16 | F23.2 |
|-------|-------|-------|-------|
| Vβ8−  | −     | −     | −     |
| Vβ8+  | +     | +     | +     |
| Vβ8.1 | +     | +     | −     |
| Vβ8.2 | +     | +     | +     |
| Vβ8.3 | +     | −     | −     |

The purified CD4+ T cells bearing different TCR Vβ8 chains are stimulated by SEB and APC and used as vaccines to be injected into B.10. PL mice.

Vaccinating B.10.PL Mice:

$1 \times 10^6$ vaccinating T cells are irradiated (3000R) and injected into B.10.PL mice intravenously; 7 days later, the vaccinated mice are challenged with 1–9 Nac of MBP peptide as indicated before. The protective effect of vaccination by CD4+Vβ8+T cells is assessed by comparing EAE symptoms of mice vaccinated with Vβ8+ or Vβ8−, CD4 T cells and unvaccinated mice. To prove that the protective effect is CD8+T cell mediated, one group of B.10.PL mice is depleted of CD8+ T cells 7 days after T cell vaccination and used as control. To check if the protective effect is Vβ8 family specific or only Vβ8.2 specific, different Vβ8+ T cell lines are used as vaccines. The protective effect is assayed by the comparison of EAE symptoms of different groups.

Effect of β-IFN on isolated CD8+ T cells

CD8+ T cells are isolated using magnetic beads, and checked by FACS. The cells are then incubated with β-IFN for 48 hours, either alone or in the presence of Con-A plus APC (adherent cells deprived of lymphocytes). The capacity of these cells to suppress the proliferation of T cells is then tested and compared with that of parallel cultures to which β-IFN had not been added.

Experiment 3: Demonstration that Chloroquine Eliminates the Resistance of Activated T Cells to the Kill by the CD8+ T Cells Six groups of Balb/c mice (6 mice each) were treated (FIG. 2) as follows: 1) daily injections of PBS (phosphate buffered saline) for 14 days (●—●, Control) 2) daily injections of 1 mg Chloroquine base (0———0, CHQ) 3) One i.v. injection of 50 μg SEB on day 0 (△—△, SEB) 4) daily injections of 1 mg chloroquine base, plus one i.v. injection of 50 μg SEB on day 0 (x———x, SEB-CHQ) 5) 50 μg SEB on day 0 mice depleted of CD8+ T cells, depletion performed as described in reference 4 (□———□, CD8 depleted SEB) 6) 50 μg SEB on day 0 in mice depleted of CD8+ T cells and treated with daily injections of 1 mg chloroquine base (†———†, CD8 depleted-SEB-CHQ).

TABLE 2

The effects of treatment on the percentage of CD4+ cells expressing Vβ8 T cell receptor chain.

|                  | CD4  | Vβ81.2 | %    | Vβ6  | %    | CD8  | Vβ81.2 | %    | Vβ6  | %    |
|------------------|------|--------|------|------|------|------|--------|------|------|------|
| Control          | 43.0 | 11.2   | 19.0 | 4.8  | 11.2 | 11.2 | 3.91   | 34.9 | 1.02 | 9.1  |
| SEB              | 29.5 | 5.61   | 26.0 | 4.0  | 13.6 | 19.6 | 8.54   | 43.6 | 1.5  | 5.8  |
| SEB/Choroquine   | 30.3 | 6.46   | 21.3 | 3.55 | 11.7 | 23.0 | 10.5   | 45.6 | 1.35 | 5.9  |
| Control          | 40.8 | 7.0    | 17.2 | 4.86 | 11.9 | 10.2 | 3.69   | 36.2 | 0.98 | 9.6  |
| SEB              | 38.0 | 6.04   | 15.9 | 4.47 | 11.8 | 14.4 | 5.39   | 37.4 | 1.17 | 8.1  |
| SEB/Choroquine   | 37.6 | 4.78   | 12.7 | 5.11 | 13.6 | 15.6 | 5.31   | 34.0 | 1.64 | 9.0  |
| Control          | 45.4 | 7.92   | 17.5 | 5.2  | 11.5 | 10.8 | 3.25   | 30.1 | 0.98 | 9.1  |
| SEB              | 32.7 | 4.19   | 12.8 | 4.78 | 14.6 | 13.0 | 4.42   | 34.0 | 1.25 | 9.6  |
| SEB/Choroquine   | 38.9 | 3.69   | 9.4  | 5.71 | 14.7 | 9.81 | 2.67   | 27.2 | 1.09 | 11.1 |

Figure 2:
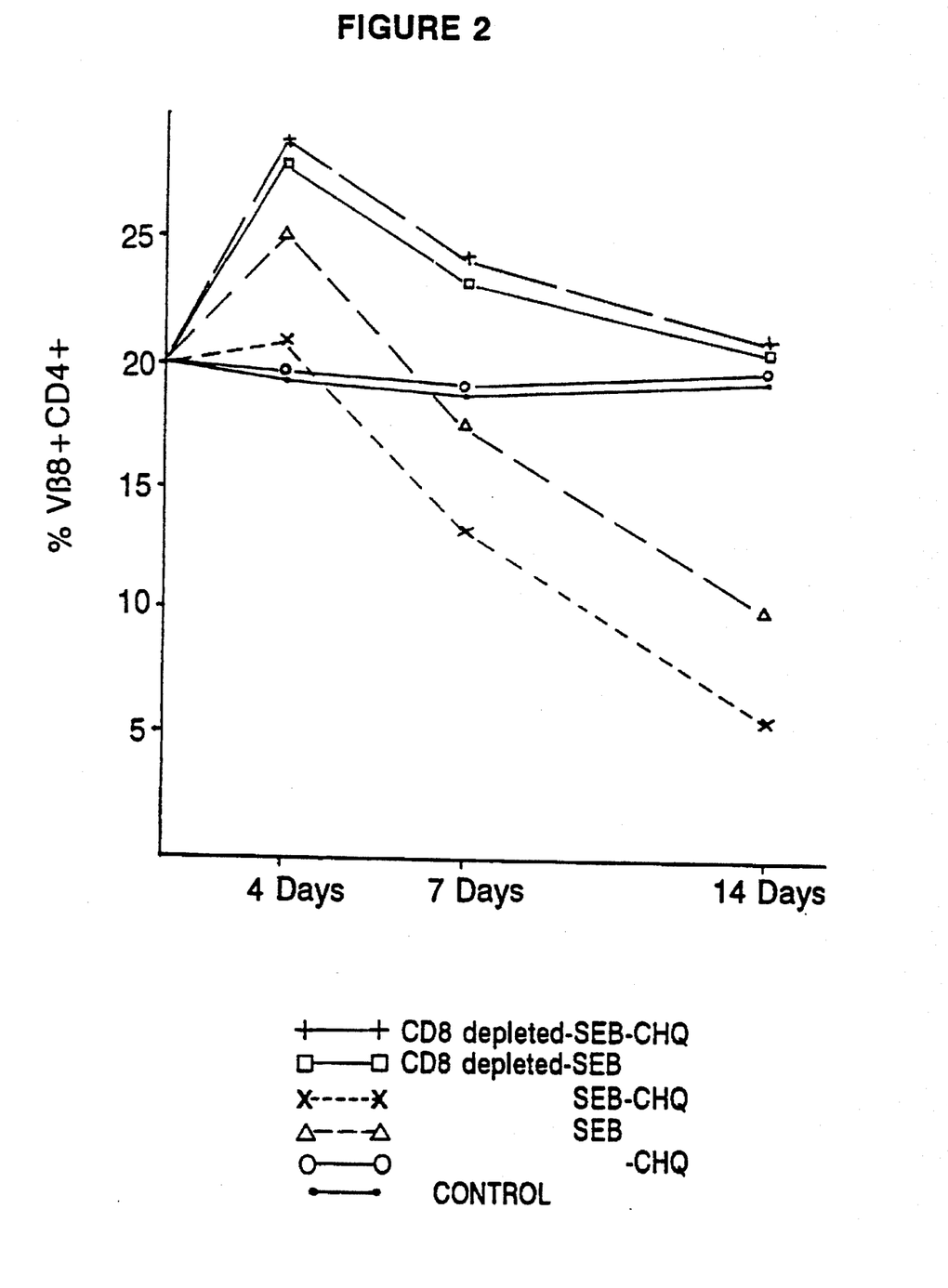

The effects of these treatments on the percentage of CD4+ cells expressing Vβ8+ T cell receptor chain are shown in FIG. 2 and Table 2. It is apparent that chloroquine alone did not affect the T cells. SEB alone induced an increase of Vβ8+ CD 4+cells, followed by a fall, as in the previous experiments (see FIGS. 1A–1B). Chloroquine treatment eliminated the initial increase and enhanced the subsequent fall; this effect of chloroquine was completely dependent of the presence of CD8+ T cells. In essence, treatment with chloroquine greatly enhances the killing of CD4+ cells by the CD8+ T cells, as induced by priming with the superantigen SEB, even in the first days after priming when, normally, the CD4+cells appear resistant to this killing. This experiment was repeated with mice treated with a lower dose of chloroquine (0.2 mg/day), with similar results.

Experiment 4: Simultaneous Treatment with Drugs that Stimulate CD8+Suppressor T Cells and Chloroquine in Human Autoimmune. Diseases.

Multiple Sclerosis (MS)

The limitation of the therapeutic effects of long-term treatment of MS with β-IPN (a CD8+ T cell stimulator) is due to the resistance of activated pathogenic CD4+ cells to the suppressive (killing) action of CD8+ T cells and that maximum benefits is obtained by eliminating this resistance with the usage of chloroquine.

In addition to continuous treatment with β-IFN, MS patients receive hydroxychloroquine (Plaquenil™) by mouth in a dosage of 400 mg/day or 10 kg/day for periods not to exceed 3–4 weeks at intervals of about 2 months, and anyway during the relapses of the disease. This dosage corresponds to the one given for prolonged period for treatment of patients with rheumatoid arthritis and to that employed in the hereinabove mouse experiments where an abrogation of the resistance of the superantigen-activated CD4+ T cells to the deletion by CD8+ suppressors was detected. This dosage provides a molar concentration of chloroquine in the body sufficient to interfere with the endosome function and therefore with the process of Class I MHC recycling in activated T cells, a process that may provide resistance of these cells to the effect of the TCR-restricted CD8+ killer/suppressors.

Rheumatoid Arthritis (RA)

In RA subjects, administration of both chloroquine and β-IFN is a treatment of choice. In the first treatment one may consider chronic treatment with β-IFN for periods and with a dosage already experimented in MS patients with added periods of a few weeks of hydroxychloroquine to provide suitable targets for the population of CD8 killers raised by β-IFN.

Use of chloroquine to augment the efficacy of treatments involving "T cell Vaccination"

Animal experiments [3, 12, 21, 24] have shown that "vaccination" with CD4+ T cell lines or clones whose pathogenic capacity had been inactivated with glutaraldehyde fixation or high hydrostatic pressure could stimulate "anti-idiotypic" or "anti-ergothypic" CD8+ T cells capable of exerting a protective effect in the experimental disease. The medical procedure, in humans, which is closer to "T cell vaccination" is that of "photopheresis," that involves oral administration of 8-methoxypsoralen (8-MOP) to patients, the extracorporeal irradiation with low-energy U.V. light of the lymphocytes from about 500 ml of bloods and their reinfusion in the patient.

The main target of this procedure has been the treatment of cutaneous lymphoma (Sezary's syndrome), a malignancy of CD4+ T cells. Subjects are treated with hydroxychloroquine (400 mg base equivalent/day) for a period of one-two weeks after the photopheresis treatment may provide the necessary sensitivity of the CD4+ T lymphoma cells to the killing action of the CD8+killers induced by the "T cell vaccination," necessary to obtain good results in a higher number of patients. It is interesting to point out that the cells of cutaneous lymphomas tend to express a limited range of T cell receptor variable region chains [13], and are therefore appropriate targets for Vβ-restricted CD8+ killers, as discussed in the previous sections.

Experiment 5: Demonstration that CTCL Subjects Treated with Photopheresis, Manifest CD8+ T Lymphocytes Capable of Exerting a Cytotoxic Effect on the CTCL Cells Peripheral blood mononuclear cells (PBMC) from CTCL patients at $5 \times 10^5$ cells/ml in RPM1 1640 supplemented with 10% FCS and 10 nanograms/ml human recombinant IL-7 are cultured (rIL-7 is available from GIBCO and medium changes and maintenance of the lines are done according to Dalloul et al [26]. The lines are characterized by membrane staining and analysis with the fluorescence activated cell sorter and should show the expected CD3+, CD4+, CD8–, CD7– phenotype of Sezary cells. In addition the restriction of expression of the TCR chain is also be assessed on the cell lines by membrane staining with a panel of anti Vβ antibodies (available from MAC Inc., Westbrood, Me.). In addition, the cells are flattened on glass slides, stained with May-Grunwald-Giemse and those with the morphology of Sezary cells are counted.

These cells are then labeled with $^{51}Cr$ and used as targets of autologous CD8+ T cells in a standard chromium-release assay. The target T cells form the Sezary line are labeled with 200 μl of $^{51}Cr$ for one hour, washed three times and incubated with the autologous CD8+ T cells at various effector/target cells ratio for four or eight hours. After the incubation the supernatant is harvested and radioactivity counted on a gamma counter (LKB) Y. The mean of triplicate samples are calculated and percent of $^{51}Cr$ release is determined as follows: % of $^{51}Cr$ release=100 [(experimental $^{51}Cr$ release-control Cr release)/(maximum, $^{51}Cr$ release-control Cr release)]. Experimental $^{51}Cr$ release represents counts from target T cells mixed with effector T cells; control $^{51}Cr$ release represents counts from targets incubated with medium alone (spontaneous release); maximum $^{51}Cr$ release represents counts from targets exposed to 5% Triton X-100.

Isolation of CD8+ T cells from the blood of CTCL patients

The study group is comprised of male and female subjects over 18 years of age. Women of child bearing potential must have a negative pregnancy test upon entrance to the study and agree to use an active form of birth control.

Subjects with CTCL currently receiving photopheresis are eligible to enter the study. Subjects receiving adjunctive treatment for CTCL (interferon, methotrexate, etc.) and subjects who are currently participating in other clinical trials are not eligible. Subjects who have contraindications to hydroxychloroquine (G6PD neg, abnormal eye exam) are not eligible.

The criteria used for assessing clinical effect is be a "skin score." The body surface is divided into specific quadrants. Each quadrant is assessed according to the following severity score:

```
0   - Normal Skin
0.5 - Few scattered erythematous papules
1   - Minimal erythema and edema
      No scale or fissuring
2   - Substantial erythema and edema
      No fissuring or ectropion
3   - Subreaxial erythema, Scaling and edema
      No fissuring or ectropion
4   - Most severe, universal involvement with
      maximal erythema, edema and scale;
      Fissuring or ectropion may be present
```

Each quadrant has an estimated percentage of surface area. This percentage is multiplied by the severity score for that area which gives a "regional score." Finally, all "regional scores" are added to obtain an "over score."

Subjects receive one photopheresis treatment on two consecutive days every four weeks as usual. On weeks two and three of each treatment cycle (the two weeks between photopheresis) the patients are to receive 400 mg per day of hydroxychloroquine for three cycles. T cell marker studies on peripheral blood are done monthly starting two months prior to the administration of hydroxychloroquine and continuing until two months after the last dose of hydroxychloroquine.

Assessment of a patients' skin score is made prior to each treatment cycle starting two months prior to the administration of hydroxychloroquine and continuing two months after the last dose of hydroxychloroquine.

Subjects blood is obtained four days after photopheresis during the months that hydroxychloroquine has been administered, and the mononuclear cells are separated by the standard phycoll-hypaque procedure. The cells are first depleted of adhering cells and B lymphocytes are separated by incubation with goat anti human immunoglobulin-coated beads (Advanced Magnetics, Inc.) at a ratio of 10 7/ml beads for 30 minutes at 40° C. The cells are separated from the beads by a Bio Mag Separator (Advanced Magnetics, Inc.) and the unbound cells are then positively selected for CD8+ lymphocytes by incubating with 0.1 ml of 1:40 sites of OK-T8 ATCC (anti-human CD8 hybridoma) for 30 min washing three times, and incubating with goat anti-mouse immunoglobulin coated beads for 30 minutes at 40° C. The beads separated at 37° C. and cleared from the cells that have now fallen off from the beads, by Bio Mag Separator again. The final purified population is essentially CD8+ T lymphocytes. These cells are immediately tested for cytotoxic activity against the aunologous Chromium-labeled Sezary cell lines (at various effector/target cell sections) as requested above.

Control cells are Chromium-labeled T cell lines (Jurkat and Molt$^{-3}$) as well as autologous B cell lines established by transformation with Epstein-Barr virus.

The effect of hydroxychloroquine on the sensitivity of the cells of the continuous Sezary line to the cytotoxic effect of the autologous CD8+ T cells is tested. Short term $^{51}$Cr release assay is done using labeled target cells previously treated for various periods of time with 50 mM hydroxychloroquine. Experiments are also done incubating the target and the effector cells in the presence of hydroxychloroquine.

Discussion

It has been established [11, 37, 38] that activated T cells spontaneously internalize their membrane Class I MHC molecules into acidic endosomes and then recycle them to the surface. The physiological significance of this massive cellular event (about on half of all Class I MHC molecules are recycled every hour in an activated T cell) has never been established. It has, however, been established [32, 38] that chloroquine blocks this recycling, presumably by neutralizing the acidic endosomes.

The experiments described in the preceding sections offer an understanding of the functional role of the recycling of Class I MHC molecules in activated T cells: In essence this cellular event protects the activated cells from the killing by CD8+ (suppressor) cells. Chloroquine, in concentrations sufficient to block the Class I recycling, eliminates this protection. The cytoplasm of murine T cells stimulated in vitro with the superantigen SEB has been examined by immunofluorescence and results indicated that after 3 days of culture there is a peak of endocytic activity with about 50% of all the cells (and most of the blasts showing Class I MHC in the endosomes; 80%, at least, of these cells appear to belong to those that express the Vβ8 TCR chain because they also show the presence of these molecules in the endosomes that contain Class I MHC. In the following clays the endocytic activity declines.

There is therefore a parallel between the recycling of Class I MHC seen in T cells stimulated with SEB and their increase in numbers, supporting the hypothesis that this activity protects the cells from killing by CD8+, a protection that, as already said, is abrogated by chloroquine.

The combined approach of hydroxychloroquine and IFN-β to the treatment of MS, provides periods in which the activated pathogenic cells responsible for the autoimmunity are (by chloroquine) made fully sensitive to the kill by the population of CD8+ killers that have been recruited with the treatment with β-IFN. Treatment of MS with chloroquine alone is of use, but only in those patients and in those periods where CD8+ suppressor T cells are not depressed, as they often are in MS. Treatment with chloroquine considerably increases the susceptibility of pathogenic CD4+ T cells to the killing by CD8+ T cells. On the other side treatment with β-IFN alone may have its therapeutic effects limited by the resistance of the activated, pathogenic, CD4+ T cells. Therefore, treatment with chloroquine is more effective if performed in conjunction with a stimulant of CD8+ T cells, like β-IFN.

REFERENCES

1. Abreu, S. (1982) *Immunoloqica ,Communications* 11: 1.
2. Arnason, B. G. W. (1993) *Neurology* 43: 641.
3. Ben-Nun, A., et al. (1981) *Nature* 292: 60.
4. Brooks, P. M., et al. (1986) In the Clinical Pharmacology of Anti-Inflammatory Agents, eds. Taylor and Franers, London, p. 86.
5. Connolly, K. M., et al. (1988) *Agents and Actions* 25: 1–2 and 94.
6. Dialynas, D. P., et al. (1983) *Immunol. Rev.* 74: 30.
7. Edelson, R. L. (1991) *Ann. N.Y. Acad. Sci.* 636: 154.
8. Hardy, R. R. (1986) In Handbook of Experimental Immunology 4th edn., eds. Weir, D. M, et al., London, 31: 1–31.12.
9. Haskins, K., et al. (1984) *J. Exp. Med.* 160: 452.
10. Hertz, F. and Deghenghi, R. (1985) *Agents and Actions* 16: 5.
11. Hochman, J. H., et al. (1991) *J. Immunol.* 146: 1862–1867.
12. Holoshitz, J. et al. (1983) *Science* 219: 56.
13. Jack, A. S., et al. (1990) *Am. J. Pathol.* 136: 17.
14. Jacobs, et al. (1987) *Arch. Neurol.* 44: 589.
15. Jiang, H., et al. (1992) *Science* 256: 1213–1215.
16. Kanagawa, O., et al. (1989) *J. Cell. Immunol.* 119: 412.
17. Kawabe, Y. and Ochi, A. (1991) *Nature* 349: 245–248.
18. Kawabe, Y. and Ochi, A. (1990) *J. Exp. Med.* 172: 1065–1076.
19. Koh, D. R., et al. (1992) *Science* 256: 1210–1213.
20. Ledbetter, J. A. and Herzenberg, L. A. (1979) *Immunol. Rev.* 47: 63–90.
21. Lider, O. et al. (1988) *Science* 239: 181.
22. Mackenzie, A. H. (1983) *Am. J. Med.* 75: 48–58.
23. Maksymowych, W. and Russel, A. S. (1987) *Semin. Arthritis Rheum.* 16: 206–221.
24. Maron, R. et al. (1983) *J. Immunol.* 131: 2316.
25. McChesney, E. W., et al. (1967) *J. Pharmacol. Exp. Ther.* 158: 323–31.
26. Moore, W. A. and Kautz, R. A. (1986) In Handbook of Experimental Immunology 4th edn., eds. Weir, D. M., et al., London, 30.1–30.11.
27. Noronha, A., et al. (1990) *Am. Neurol.* 27: 207.
28. Olsson, T. (1992) *Curr. Opin. Neurol. Neurosurg.* 5: 195–202.
29. Parks, D. R. and Herzenberg, L. A. (1989) In Fundamental Immunology 2nd edn., eds. Paul, W. E., Raven Press Ltd., New York, 781–802.
30. Paul, W. (1989) Fundamental Immunology, Raven Press, New York, p. 649–651.
31. Reader, A. T., and Arnason, B. G. W. (1985) In Handbook of Clinical Neurology, Demyelinating Diseases, eds. Vinken, P. J., et al., Amsterdam, Elsevier Science, 3: 337–395.
32. Reid, P. A. and Watts, C. (1990) *Nature* 346: 655.
33. Rellahan, B. L., et al. (1990) *J. Exp. Med.* 172: 1091–1210.

34. Sibley, W. A. (1992) Therapeutic Claims in Multiple Sclerosis, 3rd ed. New York, p 16.
35. Sun, D., et al. (1988) *Nature* 332: 843–845.
36. The IFNB Multiple Sclerosis Group, (1993) *Neurology* 43: 655.
37. Tse-Eng, D. and Pernis, B. (1984) *J. Exp. Med.* 159: 193–207.
38. Tse, D. B, et al. (1986) *J. Mol. Cell. Immunol.* 2: 315–329.
39. Wollheim, F. A., et al. (1978) *Scand. J. Rheumatol.* 7: 171–6.
40. Wollfgang, E., et al. (1991) *Blood* 78: 1781–1788.

What is claimed is:

1. A pharmaceutical composition which comprises an amount of chloroquine effective to block MHC Class I recycling and an amount of a CD8+ T cell stimulatory agent effective to stimulate proliferation of CD8+ T cells to a concentration such that the resulting CD8+T cells kill CD4+ T cells, and a pharmaceutically acceptable carrier.

2. The pharmaceutical composition of claim 1, wherein the CD8+ T cell stimulatory agent is interferon.

3. The pharmaceutical composition of claim 2, wherein the interferon is β-interferon.

4. A method for treating multiple sclerosis in a subject which comprises administering to the subject an amount of chloroquine effective to treat the multiple sclerosis.

5. A method for treating an autoimmune disease in a subject which comprises administering to the subject an amount of the pharmaceutical composition of claim 1 effective to treat the autoimmune disease.

6. The method of claim 5, wherein the CD8+ T cell stimulatory agent is interferon.

7. The method of claim 6, wherein the interferon is β-interferon.

8. The method of claim 7, wherein the chloroquine and the β-interferon are administered sequentially.

9. The method of claim 7, wherein the chloroquine and the β-interferon are administered simultaneously.

10. The method of claim 4, wherein administration to the subject is intratumorally, intradermal, topical, oral, intravenous, intramuscular, intratracheal, or by subcutaneous administration.

11. The method of claim 4, wherein the amount is from about 200 to about 600 mg/day of chloroquine base equivalents.

12. The method of claim 7, wherein the amount of the β-interferon is from about $1\times10^6$ to about $8\times10^6$ units per day of β-interferon.

13. A method for treating cutaneous lymphoma disease in a subject which comprises administering to the subject an amount of chloroquine effective to treat the cutaneous lymphoma disease.

14. The method of claim 13, wherein treatment further comprises treating the subject with photopheresis.

15. The method of claim 13, wherein administration to the subject is intratumorally, intradermal, topical, oral, intravenous, intramuscular, intratracheal, or by subcutaneous administration.

16. The method of claim 13, wherein the amount is from about 200 to about 600 mg/day of chloroquine base equivalents.

17. A method for treating rheumatoid arthritis in a subject which comprises administering to the subject an amount of the pharmaceutical composition of claim 1 effective to treat rheumatoid arthritis.

18. The method of claim 17, wherein the chloroquine is administered in conjunction with interferon.

19. The method of claim 17, wherein the chloroquine is administered in conjunction with β-interferon.

20. The method of claim 17, wherein the amount is from 200 to about 600 mg/day of chloroquine base equivalents.

21. The method of claim 18, wherein the amount of the β-interferon is from about $1\times10^6$ to about $8\times10^6$ units per day of β-interferon.

22. A method of depleting CD4+ T cells which comprises contacting to the cells an amount of chloroquine effective to block MHC Class I recycling and a CD8+ T cell stimulatory agent in an amount effective to stimulate proliferation of CD8+T cells to a concentration such that the resulting CD8+ T cells kill CD4+ T cells, so as to thereby deplete CD4+ T cells.

23. The method of claim 22, wherein the cells are pretreated with an antigen or mitogen prior to the administration of chloroquine and the CD8+ T cell stimulatory agent.

24. The method of claim 22, wherein the antigen is *Staphyloccus aureus* (SEB) or concanavalin A (Con A).

25. The method of claim 24, wherein the pretreatment of the cells increase expression of CD4+ T lymphocyte Vβ8 receptor expression.

26. The method of claim 25, wherein the CD8+ T cell stimulatory agent is interferon.

27. The method of claim 26, wherein the CD8+ T cell stimulatory agent is β-interferon.

28. The method of claim 5, wherein the autoimmune disease is multiple sclerosis.

* * * * *